United States Patent [19]
Little

[11] Patent Number: 4,964,149
[45] Date of Patent: Oct. 16, 1990

[54] FLUID CONTROLLED COUNTERBALANCE AND POWER-ASSIST FOR RADIATION IMAGING

[75] Inventor: Glenn A. Little, Chagrin Falls, Ohio

[73] Assignee: Picker International, Inc., Cleveland, Ohio

[21] Appl. No.: 190,833

[22] Filed: May 6, 1988

Related U.S. Application Data

[63] Continuation-in-part of Ser. No. 12,179, Feb. 9, 1987, abandoned.

[51] Int. Cl.⁵ ............................................. G03B 42/02
[52] U.S. Cl. .................................... 378/167; 378/181; 378/210
[58] Field of Search ............... 378/177, 179, 181, 193, 378/194, 195–197, 208–209, 176, 167, 210; 269/73; 91/4, 32; 60/372, 563, 565; 250/363.05, 363.08

[56] References Cited

U.S. PATENT DOCUMENTS

| | | | |
|---|---|---|---|
| 1,314,153 | 8/1919 | Schneider | 91/4 R |
| 2,526,879 | 10/1950 | Kizaur | 378/196 |
| 2,559,858 | 5/1951 | Mueller et al. | 335/27 R |
| 2,560,782 | 7/1951 | Scholz | 378/176 |
| 2,588,124 | 3/1952 | Kizaur | 378/177 |
| 2,890,346 | 6/1959 | Kizaur et al. | 378/176 |
| 2,892,947 | 6/1959 | Emanuelson | 378/197 |
| 2,909,665 | 10/1959 | Guentner et al. | 378/194 |
| 2,997,585 | 8/1961 | Schiring | 378/91 |
| 3,043,953 | 7/1962 | Craig et al. | 378/179 |
| 3,124,371 | 3/1964 | Weir | 91/4 R |
| 3,307,037 | 2/1967 | Thomas | 378/176 |
| 3,325,643 | 6/1967 | Craig et al. | 378/189 |
| 3,707,629 | 12/1972 | Colston | 378/176 |
| 3,707,630 | 12/1972 | Koerner et al. | 378/176 |
| 3,829,698 | 8/1974 | Goetz | 378/181 |
| 3,916,203 | 10/1975 | Norgren | 378/176 |
| 4,197,465 | 4/1980 | Schneider | 378/179 |
| 4,357,538 | 11/1982 | Hunt et al. | 378/175 |
| 4,439,003 | 3/1984 | Roth | 350/6.6 |
| 4,585,351 | 4/1986 | Gronek et al. | 269/73 |
| 4,602,378 | 7/1986 | Kelman et al. | 378/26 |
| 4,630,796 | 12/1986 | Kayser et al. | 248/648 |
| 4,630,942 | 12/1986 | Tsumaki et al. | 269/73 |

FOREIGN PATENT DOCUMENTS 3236116 3/1984 Fed. Rep. of Germany ...... 378/193

OTHER PUBLICATIONS

Liebel Flarsheim Installation and Service Manual for Hydrajust II Urological Table dated Jun. 1984.

Primary Examiner—Janice A. Howell
Assistant Examiner—John C. Freeman
Attorney, Agent, or Firm—Timothy B. Gurin

[57] ABSTRACT

A fluid controlled counterbalance and power-assist system for use in a diagnostic x-ray imaging system includes a first member and a second member movably mounted to said first member. A slave actuator including a reciprocal piston is selectively coupled between the first and second members. Fluid coupling ports are located on each end of the cylinder for coupling working fluid to either side of the piston. First and second master actuators each including a cylinder are located remote from the imaging system. Each master actuator has fluid coupling ports selectively located on each end of its cylinder for coupling working fluid to one side of the cylinder and control fluid to the other side. Working fluid connection lines connect one end of the slave actuator to one end of the first master actuator and connect the opposite end of the slave actuator to the second master actuator for providing working fluid flow between said actuators. The coupling port on the opposite side of the first and second master actuators are individually connected to a source of fluid pressure. A control means comprising a handle operatively connected to a power assist actuator produces first and second pressure signals proportional to force exerted on said handle. First and second pressure regulator means are adapted to respectively receive the first and second pressure signals from the control means thereby controlling the pressure to the master actuators as a function of the force exerted on said control means handle. The first and second pressure regulator means are additional adapted to receive a first and second pressure feedback signal from said working fluid lines.

19 Claims, 5 Drawing Sheets

FLUID CONTROLLED COUNTERBALANCE AND POWER-ASSIST FOR RADIATION IMAGING

This application is a continuation-in-part of U.S. Pat. application Ser. No. 012,179 filed on Feb. 9, 1987 now abandoned.

DESCRIPTION

1. Technical Field

This invention pertains to the general field of radiation imaging and more particularly to a fluid controlled counterbalance and power assist for movable assemblies in diagnostic x-ray imaging systems.

2. Background Art

In conventional radiographic and fluoroscopic (R&F) imaging systems, a tiltable table is commonly employed. An elongated flat table top is supported by a table body. The table body, in turn, is pivotally connected to a stationary base or pedestal for tiltable motion about a horizontal axis transverse to the longitudinal extent of the table top. In this fashion the table top can be tilted in either direction from its normal position in which the top surface is horizontal.

A radiographic x-ray source is mounted on one side of the table top and directs a divergent area beam of radiation through a subject under examination placed on table top. A cassette containing an x-ray sensitive phosphor screen and light and x-ray sensitive film is positioned in the x-ray path on the other side of the table top opposite the source to intercept radiation passing through the subject under examination. The cassette is placed in a cassette carriage which is movably mounted to the table body. The cassette carriage permits alignment of the cassette along the longitudinal extent of the table top.

A fluoroscopic x-ray source is commonly mounted in the table body and directs a divergent area beam of radiation up through the table top and the subject under examination. A fluoroscopic imaging system is mounted on the opposite side and above the subject to receive the pattern of radiation emerging from the subject. The fluoroscopic imaging system includes known means for producing a substantially real time, continuous image of the internal structure of the subject under examination.

The fluoroscopic imaging system often includes additional apparatus for making a film record of the fluoroscopically produced image. These devices, known as spotfilmers or spotfilm devices generally include a cassette carriage movably supported within a housing The cassette carriage assembly supports and transports the film cassette to one of a plurality of positions within the housing.

Other devices known as spotfilm cameras and cine cameras are removably mountable to the fluoroscopic imaging assembly to acquire multi-format film images.

In order to be able to position the fluoroscopic imaging system at any desired position over the table top and to any selected distance from the table top, three mutually orthogonal axis of motion are provided. A tower assembly is movably mounted to the table body. The fluoroscopic x-ray source and the fluoroscopic imaging system are mounted to the tower assembly for movement parallel to and along the longitudinal extent of the table top. The fluoroscopic imaging system is in turn mounted to the tower via an image system support frame which permits vertical motion of the imaging system with respect to the tower assembly when the table top is horizontal. Finally, the imaging system is movably mounted to the support frame for motion along a horizontal axis transverse to the table top.

These three rectilinear paths of travel permit the fluoroscopic imaging system to be moved to any selected position over the table top and to any selected distance from the top within the limits of the respective paths of travel.

The total weight of the fluoroscopic imaging system is in excess of 400 pounds. As a result, the acceleration and frictional forces in moving the apparatus along the three paths of travel are quite high. Additionally, when the table top is horizontal, the vertical motion of the fluoroscopic imaging system must be counterbalanced against gravity. Also, when the table top is tilted from the horizontal, the vertical weight component of the fluoroscopic imaging system and x-ray source must be counter-balanced against gravity in order to achieve longitudinal movement. When the table top is tilted from the horizontal, additional counterbalance must be provided for the radiographic film cassette and its associated carriage to balance its vertical weight component against gravity and to assist in its longitudinal motion.

The counterbalancing described above is typically achieved through lead weights carried in the table body or in the tower assemblies and support frame. Since the motion of the imaging system with respect to the tower is vertical when the table top is horizontal, counterbalancing weights are carried in the tower to facilitate this vertical movement. Thus, one pound of weight supported by the tower will, with a one-to-one mechanical advantage, require one pound of counterweight and therefore two pounds of imaging system and tower weight.

Since the tower with fluoroscopic imaging system attached is movable in a vertical path when the table top is in a vertical position, weights to counterbalance the tower/imaging system are provided in the table body. The tower/imaging system counterbalancing weights must include one pound for each pound of tower/imaging system weight. Thus one pound for each pound of tower and one pound for each pound of counterbalance weight. With a one-to-one mechanical advantage in the counterweight carried in the table body as well as those in the carriage, it will be seen that for every pound of weight supported by the tower, three pounds of counterbalancing weight must be added to the table.

If additional equipment is desired to be added to the fluoroscopic imaging system, such as additional spotfilm cameras, the added counterweight required to offset the camera weight may exceed the maximum weight limit which can be carried by the table structure.

Many solutions have been proposed to solve the counterbalancing problem. One such solution is to provide a ceiling mounted counterweight which supports the weight of the spotfilmer and other devices. Such a system is described in U.S. Pat. No. 2,997,585 to Schiring and owned by the present assignee.

Another proposed solution is to provide a two-to-one mechanical advantage thereby reducing the counterweight requirements. One such system is described in U.S. Pat. No. 3,916,203 to Norgren and owned by the present assignee Yet another proposed solution is to provide a three axis pneumatic power assist system adapted for moving the spotfilm device on an x-ray table. Such a system is described in U.S. Pat. No. 3,707,629 to Colston and U.S. Pat. No. 3,707,630 to Koerner et al. This system suffers from the disadvantage of not being able to automatically compensate for variations in weight due to the addition or deletion of components or due to weight shifts in a tiltable table system. Also the power assist only provides one degree of assist, i.e., when the operator attempts to move structure more rapidly, the system does not provide additional assist in response to the operators efforts.

It is therefore an object of this invention to provide a fluid controlled counterbalance and power-assist system which eliminates the need for substantially all counterweights in the table body, automatically compensates for variations in the weight to be counterbalanced and also provides a variable, operator responsive power assist.

DISCLOSURE OF THE INVENTION

The above stated disadvantages of the prior art are reduced or eliminated by the provision of a diagnostic x-ray imaging system having a first member and a second member movably mounted to the first member. A slave actuator including a cylinder and a reciprocating piston is coupled between the first and second members The cylinder has fluid coupling ports selectively located on each end of the cylinder for coupling working fluid to either side of the piston. First and second master actuators each including a cylinder defining an air-hydraulic fluid interface, are mounted remote of the imaging system. Fluid coupling ports are selectively located on each end of the cylinders for coupling working fluid to one side of the piston and control fluid to the other side of the piston. Working fluid connection lines connect a coupling port on one end of the slave actuator to a coupling port on one end of the first master actuator and connect a coupling port on the opposite end of the slave actuator to a coupling port of the second master actuator for providing working fluid flow between the actuators. A control fluid pressure source is connected to the coupling ports on the opposite side of the first and second master actuators via control fluid pressure connection lines.

A control means including a handle operatively connected to a power assist actuator is provided for producing first and second pressure signals proportional to force exerted on the handle. First and second pressure regulator means are respectively interposed in the control fluid pressure connection lines corresponding to the first and second master actuators, and are adapted to respectively receive the first and second pressure signals from the control means for controlling the pressure to the master actuators as a function of the force exerted on said control means handle.

In a more limited aspect of the present invention the power assist actuator includes a cylinder, a piston slidable mounted in the cylinder, bias means coupled to the piston for maintaining the piston in a null position, fluid coupling ports selectively located on each end of the cylinder for coupling each side of the actuator to one of the first and second pressure regulators.

In yet another aspect of the present invention the first and second pressure regulator means are additionally adapted to receive a first and second pressure feedback signal from the working fluid lines.

In an alternate aspect of the present invention a diagnostic x-ray imaging system is provided which includes a fluid controlled counterbalance system. The system includes a first member and a second member movably mounted to the first member A slave actuator comprising a cylinder and a reciprocating piston is selectively coupled between the first and second members. A fluid coupling port is located on at least one end of the cylinder for coupling actuating fluid to one side of the piston. A master actuator is located remote from the first and second members, and includes a cylinder, a reciprocal piston and a fluid coupling port located on at least one end of the cylinder for coupling actuating fluid to one side of the piston. Means is provided for connecting the fluid coupling ports for fluid communication between the master and slave actuators. A piston extension means is provided and has one end secured to one side of the master actuator piston and the other end extending beyond the adjacent end of the master actuator cylinder A balancing weight means is coupled to the extending end of the piston extension means thereby causing the piston to exert pressure on the actuating fluid.

One advantage of the present invention is to provide a counterbalance system for movable assemblies in a diagnostic imaging system that results in elimination in substantially all counterweights from the system structure itself.

Another advantage of the present invention is that the degree of counterbalance force automatically adjusts when the weight of the component being balanced changes Yet another advantage of the present invention is that it provides dynamic variation in the counterbalance force as system components rotate against gravity.

A further advantage of the present invention is that it provides a power-assist that is continuously variable by the operator.

These and still further advantages will become apparent to those of ordinary skill in the art upon reading and understanding the following detailed description of the preferred embodiment.

BRIEF DESCRIPTION OF THE DRAWINGS

The invention may be embodied in various steps and arrangement of steps and components and arrangement of components. The drawings are only for the purpose of illustrating a preferred embodiment and are not to be continued as limiting the invention.

BEST MODE FOR CARRYING OUT THE INVENTION

Figure 1:
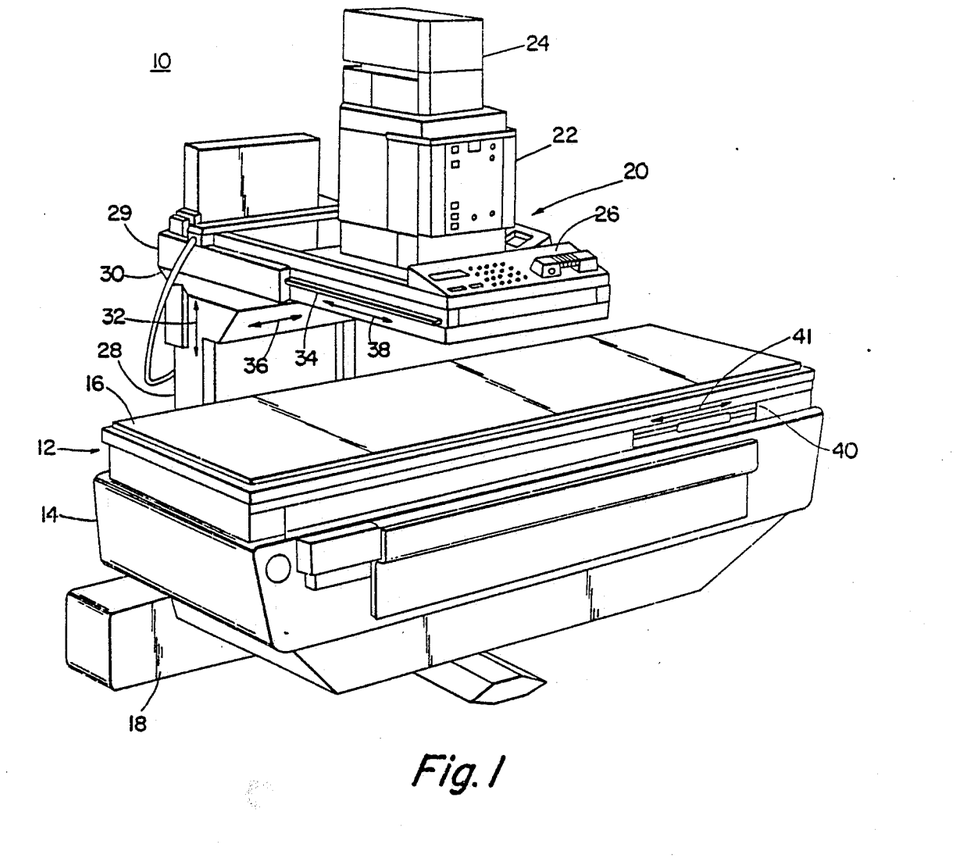
FIG. 1 is a perspective view of a fluoroscopic imaging system and radiographic spotfilm device on a tiltable x-ray table in which the present invention is incorporated.

While the following description is in terms of a tiltable radiographic and fluoroscopic (R&F) imaging system including a spotfilm device, it is to be understood that the present invention has utility in non-tilting radiographic systems or in fluoroscopic systems without a spotfilm device where movable structure is provided Referring to the figures and particularly FIG. 1, a R&F imaging system 10 is shown in which the present invention is incorporated. An examination table 12 includes a hollow, tub-shaped body 14 and an elongated table top 16 for supporting a subject or patient under examination (not shown).

The table body 14 is rotatably supported in known fashion by a main support structure or pedestal, a portion of which is indicated at 18. The table 12 can be rotated about a horizontal axis perpendicular to the longitudinal extent of the table top 16 in either direction from its normal position (as shown) wherein the top surface is horizontal. In so-called 90/90 tables, the table is tiltable in either direction 90° from the horizontal. Other tables are tiltable in one direction from horizontal to a 90° or vertical position and in the other direction to a so-called Trendelenburg position wherein the angle of tilt is limited to 45° or less from the horizontal.

A fluoroscopic imaging system shown generally at 20 is commonly comprised of an image intensifier tube assembly 22, television camera assembly 24 mounted to view the output of the image intensifier tube, and spotfilm device 26. The imaging system 20 is supported above the table top 16 by a vertical tower assembly 28. The tower assembly is supported for longitudinal movement along the table body 14 by a tower support carriage (not shown). A fluoroscopic x-ray source (not shown) is mounted to the tower support carriage within the table body. In this fashion, the x-ray source and the fluoroscopic imaging system move in unison along the longitudinal extent of the table top thereby maintaining alignment between the fluoroscopic imaging system and x-ray tube regardless of longitudinal position This longitudinal motion is depicted by arrows 36.

The entire fluoroscopic imaging system 20 is attached to the tower 28 by an imaging system support frame 29 that includes a pair of transverse extending arms, one of which is shown at 30. The support frame 29 and thus arms 30 are mounted for motion relative to the tower 28 along an axis perpendicular to the plane of the table top and provide means for adjusting the height of the imaging system 20 above the table top 16. This relative motion is indicated by arrows 32.

The imaging system 20 is slidably attached to the arms 30 by a pair of support rails, one of which is shown at 34. The support rails 34 extend along the sides of the spotfilm device 26 and provide for movement normal to the longitudinal extent of the table top. This lateral or transverse motion is depicted by arrows 38.

Specific detail for implementing the conventional motions described above can be found in the following U.S. patents owned by the present assignee and which are hereby incorporated herein by reference:

U.S. Pat. No. 3,916,203 to Norgren entitled "X-ray Apparatus Including Counterbalancing Mechanism For Spotfilmer and the Like";

U.S. Pat. No. 4,197,465 to Schneider entitled "X-ray Table"; and

U.S Pat. No. 4,357,538 to Hunt et al. entitled "Spotfilming Apparatus and Methods."

The above described R&F imaging system is also capable of radiographic examinations. An overtable radiographic x-ray source (not shown) is commonly employed and directs a divergent area beam of radiation downward through the patient under examination. The radiographic x-ray source is typically mounted in known fashion on a tube support carriage attached overhead to a ceiling support structure. A cassette containing x-ray and light sensitive film is positioned in the x-ray path below the table top in a cassette carriage shown generally at 40. The cassette carriage is typically a metal tray with means to clamp and center the cassette in place The tray is supported for longitudinal movement beneath the table top 16 by the table base 14. This longitudinal motion is indicated by arrows 41. The tray is also movable in a transverse direction with respect to the table top for loading and unloading the x-ray film cassette An example of one such cassette carriage can be found in U.S Pat. No. 3,829,698 to Goetz entitled "X-ray Apparatus with Improved Film Cassette Clamping and Size Sensing Means" owned by the present assignee and incorporated herein by reference.

In general, relative motion between two components is hereinafter described. For the purpose of clarity, the base or reference component is referred to as a first member and the component movable relative to the reference component is referred to as a second member.

It can be readily seen from the above description that when the table 12 is in the horizontal position, vertical motion of the imaging system 20 (arrows 32) is possible only if the weight of the imaging system 20 is counterbalanced against gravity. When the table 12 is tilted from the horizontal, longitudinal motion of the fluoro imaging system 20 (arrows 36) and the cassette carriage 40 (arrows 41) can be easily obtained only if the vertical weight component of the system 20 or the carriage 40 is counterbalanced against gravity. Also, due to the frictional and acceleration forces required to move the various apparatus from their "at-rest" positions, a power assist is desirable to aid in the operation of the equipment.

The present invention provides a fluid controlled counterbalance and power-assist assembly individually for the tower assembly 28, the imaging system support frame 29 and the spotfilm device 26 so that the three orthogonal axes of motion describe above are easily accomplished by the operator with only a small actuating force in any direction. Additionally, counterbalance and power-assist may also be provided for the cassette carriage 40, table top 16 (if movable with respect to table body 14), the ceiling supported radiographic x-ray tube carriage or any other complement of components that exhibit relative motion with respect to one another. Since the description for each of the counterbalance and power assist assemblies for each motion is comprised of like components and operate in like fashion, only the assembly for the longitudinal motion of the fluoro imaging system 20 is described. It is to be noted, however, that once given the following description, mere mechanical expedience within the ability of one skilled in the art is all that is required to couple the respective assemblies to the proper elements in the proper manner to achieve fluid controlled counterbalance and power assist for the other components.

Figure 2:
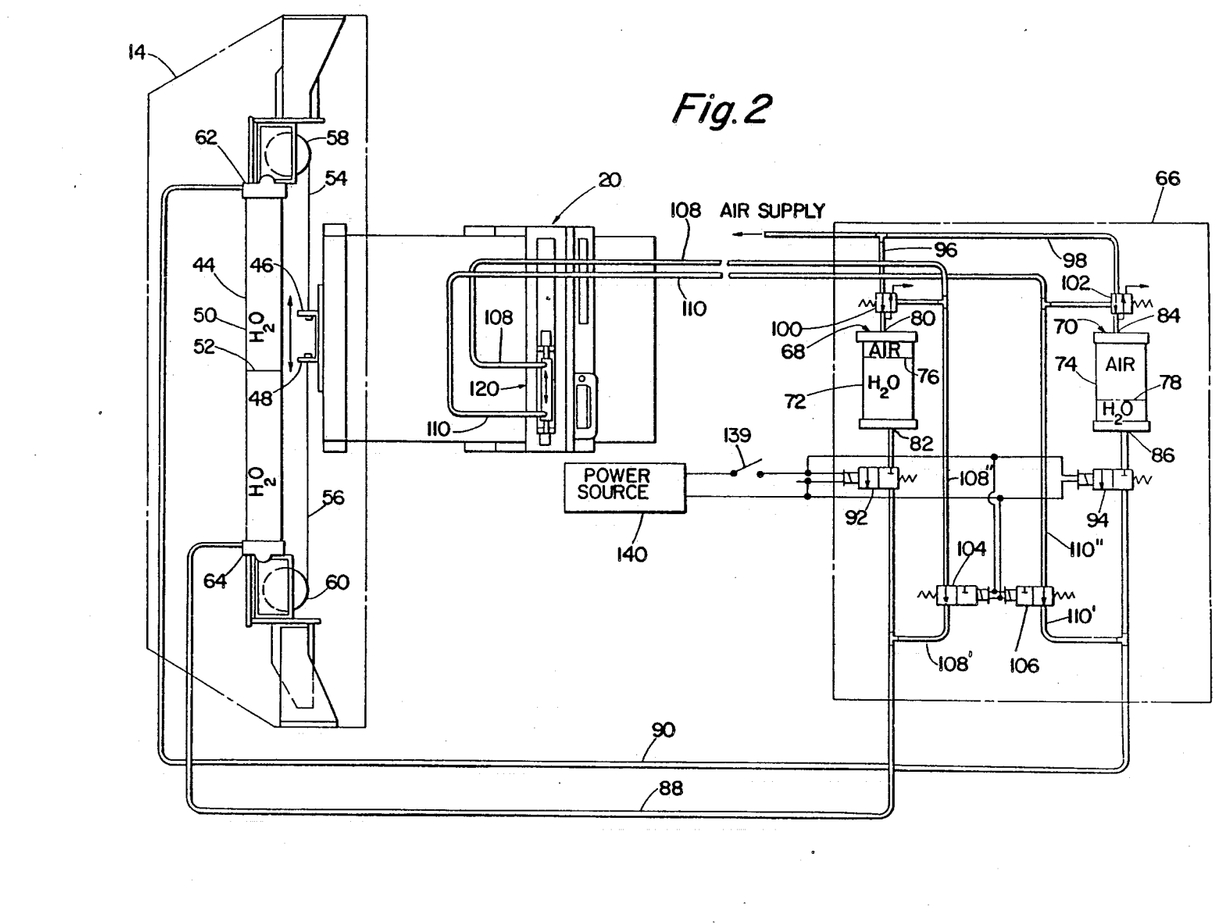
FIG. 2 is a schematic representation of the fluid controlled counterbalance and power assist circuit of the present invention.

In FIG. 2 a schematic representation of the fluid controlled counterbalance and power assist of the present invention is shown.

A slave actuator 44 is fixedly mounted to a first member (the table base 14 in this example) and is coupled to a second member (the tower 28 in this example) by means of a cable and pulley assembly internally connected to a piston 52. The cable assembly connects to brackets 46, 48.

Slave actuator 44 includes a cylinder 50 enclosing a reciprocating piston 52 which is attached on either side to cables 54, 56 and suitable seals forming a fluid tight closure on the ends of the cylinder 50. The cylinder 44 is preferably a Tol-o-matic continuous cable positioning piston. The bore of the piston, i.e. its internal diameter, is to be selected depending on the overall weight to be balanced and the pressure under which the system is to operate. Cable 54 attached to one side of piston 52 extends through one end seal and around a pulley 58 and is connected to an angle bracket 46 which is secured to the tower assembly 28. In the same manner, cable 56 attached to the other side of piston 52 extends through the other end seal and around a pulley 60 and is attached to a second angle bracket 48 which is adjacent the bracket 46.

Slave actuator 44 is filled with a non-compressible fluid referred to herein as working fluid which can be hydraulic fluid, oil, water or other suitable fluids. Movement of piston 52 is caused by the difference in working fluid pressure on each side thereof On each end of cylinder 44, a port 62, 64 is provided for the passage of working fluid in to or out of the cylinder by means of suitable couplings.

A master power control console 66 is provided remote from the imaging system 10. First and second double acting, master actuators 68, 70 are provided to feed and control the slave actuator 44. Each of the master actuators respectively include a cylinder 72, 74. On each end of cylinders 72, 74 a port is provided for the passage of a fluid in to or out of the ends of the respective cylinder A fluid is coupled to cylinder 72 by means of coupling ports 80, 82. Likewise, a fluid is coupled to cylinder 74 by means of coupling ports 84, 86.

In the preferred embodiment first and second master actuators 68, 70 are air-hydraulic separators, i.e. an air-hydraulic fluid interface is produced inside the cylinders 72, 74. This interface is shown generally at 76, 78. Suitable air-hydraulic separators are available from Tol-o-matic.

The hydraulic-fluid side or working fluid side of interface 76 of first master actuator 68, i.e., coupling port 82, is connected to coupling port 64 of the slave actuator 44 via a working fluid connection line 88. Likewise, the hydraulic-fluid side or working fluid side of interface 78 of second master actuator 70, i.e., coupling port 86, is connected to coupling port 62 of the slave actuator 44 via another working fluid connection line 90. Working fluid connection lines 88, 90 are standard ¼" O.D. hydraulic tubing.

Main solenoid valves 92, 94 are respectively interposed in working fluid lines 88, 90 to selectively block fluid flow in the lines. The function and manner of actuation of the valves 92, 94 is discussed in more detail below.

The air side or control fluid side of interfaces 76, 78 of first and second master actuators 72, 74 is connected to a control fluid pressure source which is preferrably a pressurized air supply (not shown) via control fluid pressure connection lines 96, 98 Control pressure lines are standard ¼" O.D. pneumatic tubing The preferred air supply is capable of delivering 120 psi at 10 scfm. First and second air pressure regulators 100, 102 are respectively interposed in the control lines 96, 98. The air pressure regulators act to control the air pressure to the master actuators in response to a control signal which is described in more detail below. First and second air regulators 100, 102 each include three ports. The first or input port receives unregulated supply pressure from the control fluid pressure source. The second or output port presents a regulated control fluid pressure to each of the master actuators. The third or signal port receives a pressure feedback signal, a change in which causes a proportional change in the regulated control output pressure Air regulators 100, 102 are commercially available from Fairchild, Bosch, Bellofram and other sources, and are preferably Bellofram type 20 HR air relays.

The hydraulic circuit so far described is sufficient to provide a counterbalance function and power assist. Main solenoid valves 92, 94 are normally closed, and no fluid flow in working fluid lines 88, 90 is possible thereby preventing any movement of piston 52. In this fashion, the fluoro imaging system 20 is locked in place, (i.e., counterbalanced) irrespective of table tilt position.

If the main solenoid valves are opened however, fluid communication between the first and second master actuators 68, 70 and the slave actuator 44 is possible In operation and by way of example, as air pressure to first master actuator 68 via first regulator 100 is increased, the air pressure internal to cylinder 72 will increase. Increased air pressure will likewise cause increased working fluid pressure via air-hydraulic fluid interface 76 on the corresponding side of piston 52 of slave actuator 44. If the pressure increase is sufficient to overcome the gravitational and frictional forces of the fluoro imaging system 20, longitudinal motion will occur. The movement of piston 52 will cause increased working fluid pressure on its opposite side thereby causing a corresponding increase in control fluid pressure on the control fluid side of air-hydraulic interface 78 of second master actuator 70. The increase in control fluid pressure is vented to atmosphere via second regulator 102.

In order that the operator has a variable power assist capability, a control means 120 is provided. The control means 120 is preferably mounted to the spotfilm device 26 or other suitable location Referring to FIGS. 3, 4 and 5, the control means includes a power assist actuator 121 comprising cylinder 122 enclosing a reciprocating piston 123. On each side of piston 123, rigid piston rods 124 and 124' are attached Actuator 121 is preferably a 1" Nopak piston with a 3" stroke available from Galland Henning Nopak Inc., Milwaukee, Wisconsin. Rods 124, 124' extend beyond the corresponding end of cylinder 122 through suitable seals forming a fluid tight closure on the ends of cylinder 122.

Actuator 121 is mounted to a rigid back plate 125. The length of backplate 125 is greater than the longitudinal dimension of cylinder 122 but shorter than the distance between the extending ends of rods 124, 124'. Actuator 121 is centrally mounted along the longitudinal axis of backplate 125. A portion of the backplate thus extends beyond each end of the cylinder 122 and are shown generally at 126, 126'. A pair of forward extending arms are fastened to each of the extending backplate portions. An upper forward extending arm 127 is mounted to extending backplate portion 126 above piston rod 124 and a lower forward extending arm 128 is mounted to the backplate below piston rod 124 creating a clearance space for rod 124 to extend therebetween (see FIG. 4). A pair of forward extending arms 127', 128' are likewise mounted to extending backplate portion 126' above and below piston rod 124'. The arms are mounted along the longitudinal dimension of the backplate to create a space, shown generally at 129, 129' between one side of arms 127, 128 and 127', 128' respectively and the ends of cylinder 122. The purpose of space 129, 129' is described in more detail below.

A forward extending handle member 130 is mounted between forward extending arm 127, 128 for pivotal motion about pivot axis 131. The end of handle member 130 mounted between forward extending arms 127, 128 is forked. An upper tine 132 fits between forward extending arm 127 and piston rod 124 and a lower tine 133 fits between forward extending arm 128 and piston rod 124. The space between the tines is sufficient to avoid interference with the piston rod 124 during pivotal motion of handle member 130. A similarly fashioned handle member 130' is mounted to the forward extending arms 127', 128' to pivot about pivot axis 131'. The opposite ends of handle members 130, 130' are pivotally connected in known fashion to a handle bar 138. Lateral movement of handle bar 138 thereby induces pivotal motion of handle members 130, 130' about pivot axes 131, 131' respectively (see FIG. 5).

Figures 3, 4:
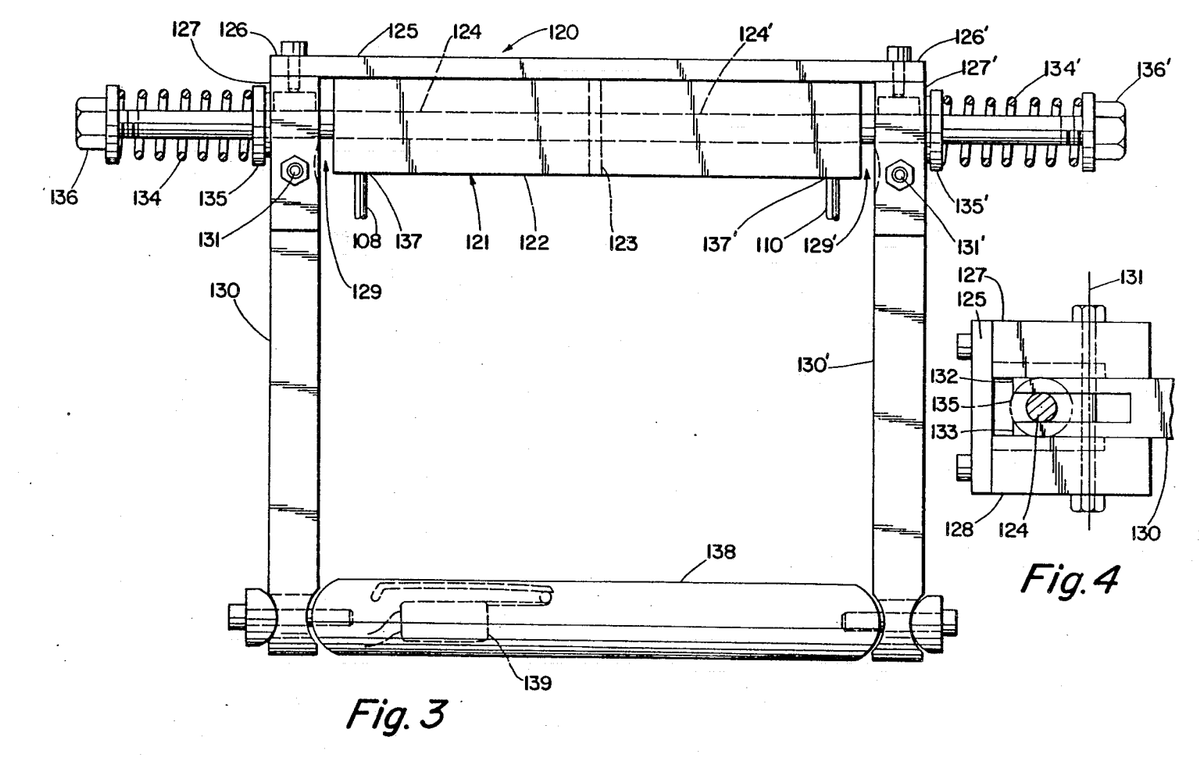
FIG. 3 is a detail view of the control means of the present invention.
FIG. 4 is a side view of a portion of the control means depicted in FIG. 3.
Figure 5:
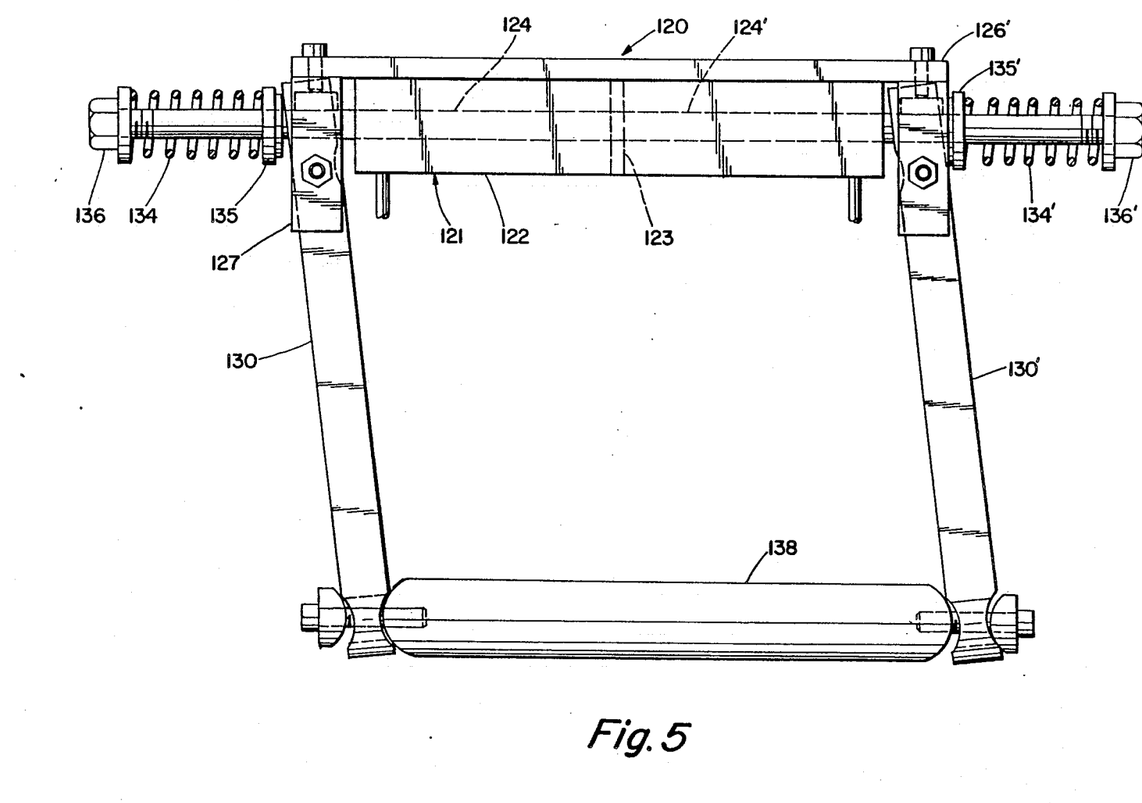
FIG. 5 is a detail view of the control means depicted in FIG. 3 with handle bar laterally displaced to an exemplary offset position.

Compression springs 134, 134' are respectively placed about the portion of rods 124, 124' which extend beyond forward extending arm 127, 128 and 127', 128'. A washer 135, 135' having an outside diameter slightly less than the space between forward extending arms 127, 128, 127', 128', forms an interface between the springs 134, 134' and the tines 132, 133 and 132', 133' respectively. The washer is preferably made of rigid nylon material and forms a smooth bearing surface for the tines as explained below. The springs 134, 134' are compressed and held in place by a washer and nut combination 136, 136' bolted to a threaded end of rods 124, 124' respectively The springs 134, 134' coact with rods 124, 124' and handle members 130, 130' to bias the piston 123 in a null position The term "null" is not intended to imply that the pressure across piston 123 is zero, but to indicate that power assisted motion has not been called for and that the pressure across piston 123 has not been changed by operation of the control means described below.

On each end of cylinder 122, a port 137, 137' is provided for the passage of actuator fluid into or out of cylinder 122 on the respective side of piston 123 Actuator fluid connection lines 108, 110 respectively connect ports 137, 137' to the signal ports of regulators 100, 102. The actuator fluid contained in cylinder 122 and lines 108, 110 is the same type of fluid, e.g., water, as is contained in slave actuator 44

Handle bar 138 includes an internal microswitch 138 which changes state when the handle is grasped by the operator. When handle bar 138 is grasped, main solenoid valves 92, 94 are activated to open and pilot valves 104, 106 are activated to close as the solenoid coils are supplied with current from a suitable power source 140. The purpose and function of valves 104, 106 and their associated lines 108', 108", 110' and 110" are explained in more detail below. Actuator fluid lines 108, 110 are now completely isolated and pressure within these lines is maintained and controlled by cylinder 122 of control means 120.

When the operator desires power assisted motion, the handle bar 138 is grasped and either pushed or pulled laterally to an offset position. An example of one such position is shown in FIG. 5. As the handle bar 138 is moved laterally, handle members 130, 130' pivot about pivot axis 131, 131' in unison and in the same direction. It is to be noted that microswitch 139 could be alternately configured to toggle upon lateral movement of handle bar 138. Referring to FIG. 5, as the pivotal motion depicted occurs, handle member 130 acts as a lever arm forcing tines 132, 133 to press against washer 135 further compressing spring 134. On the other side of actuator 121, tines 132', 133' pivot away from washer 135' into space 129' allowing spring 134' to relax. This force differential created between the springs 134, 134' causes piston 123 to exert a greater pressure on the actuator fluid in line 108 and to reduce the pressure in line 110 thereby developing first and second pressure signals. These pressure signals are fed back via lines 108, 110 and sensed by the respective air regulators 100, 102 and either add to or vent air from the appropriate master actuator 68, 70. The change in pressure in master actuators 68, 70 causes a pressure differential across piston 52 of the slave actuator 44 causing piston 52 to move. Movement of piston 52 in turn causes movement of, for example, the fluoroscopic imaging assembly 20.

Response of the system is substantially linear and proportional, i.e., the force exerted by the operator on handle 138 translates to a proportional increase in the pressure of the appropriate working fluid line. From this relationship, it is to be appreciated that the operator can call for a greater power-assist (and therefore faster motion) simply by exerting greater pressure on handle bar 138.

The system of the present invention is also capable of automatic adjustment in variations in weight experienced by slave actuator 44. For example, table tilt motion from a horizontal to a vertical or Trendelenburg position will cause a like variation in the vertical weight component of the imaging system 20. Taking the two extremes, when the table is horizontal, actuator 44 experiences no weight from the fluoro imaging system and only a power-assist to help overcome the frictional and acceleration forces required to move the imaging system 20 from an at-rest position is required.

At the other extreme, when the table is in the vertical position, the entire weight of the fluoro imaging system 20 must be counterbalanced against gravity. In intermediate positions the amount of counterbalance force required varies as a function of angular position of the table. Variations in the counterbalance force must take place dynamically as the table tilts To accommodate for these dynamic weight variations, pilot solenoid valves 104, 106 respectively provide a feedback mechanism to the air regulators 100, 102. Each of working fluid lines 88, 90 are tapped between the main solenoid valves 92, 94 and the slave actuator 44 to sample the pressure in each line thereby developing first and second pressure feedback signals For example, a pilot line 108' interconnects working fluid line 88 to the input of pilot solenoid 104. The output of pilot solenoid 104 is interconnected to the signal port of regulator 100 via a pilot line 108". Pilot solenoid 106 interconnects with working fluid line 90 and regulator 102 in the same fashion via pilot lines 110' and 110". The pilot lines are standard ¼" O.D. pneumatic tubing.

In operation, the main solenoid valves 92, 94 are normally closed and the pilot solenoid valves 104, 106 are normally open. As the table tilts from horizontal to vertical, the load on slave actuator 44 changes Depending on the direction of table tilt, one side of piston 52 will experience an increase in pressure while the other side will experience a decrease causing a like pressure variations in working fluid lines 88, 90. These pressure variations are fed back to regulators 100, 102 through pilot solenoids 104, 106 as a first and second pressure feedback signals. The regulators cause air to be pumped in to or vented from the control fluid side of master actuators 68, 70 in response to the first and second pressure feedback signals thereby maintaining pressure equilibrium throughout the system. It is to be noted that similar system action occurs when weight is either added or deducted from the imaging system as when spotfilm or cine cameras are attached.

It is to be observed that the pressures in working fluid lines 88, 90 are also present in lines 108, 110 when valves 104, 106 are open. Therefore any pressure differential across piston 52 will appear across piston 123 causing it to move against the coacting force of springs 134, 134'. Any additional movement of piston 123 caused by the operator laterally displacing handle bar 139 modifies the differential to develop the first and second pressure signal for power assisted motion, as described above.

Figure 6:
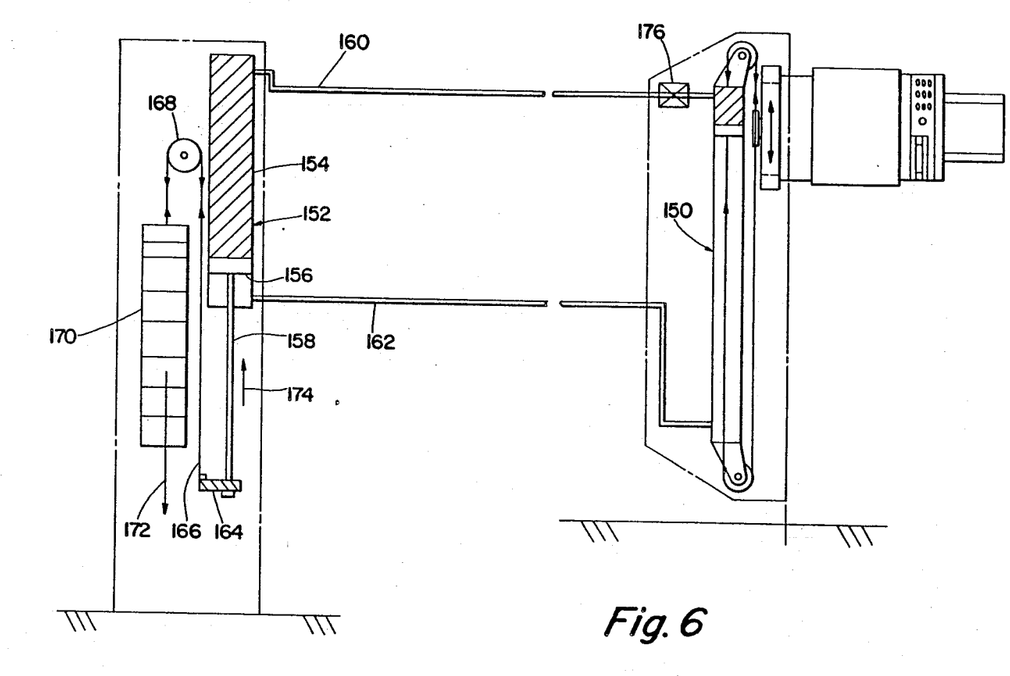
FIG. 6 is schematic representation of an alternative embodiment of a fluid controlled counterbalance system.

An alternate embodiment of a hydraulic counterbalance system is shown in FIG. 6. This embodiment finds particular utility in non-rotating systems or in systems that the weight to be counterbalanced is not expected to change.

A slave actuator 150 (substantially identical to slave actuator 44) is mounted in the table body and is interconnected to the tower assembly in same fashion as described above. A master actuator 152 is mounted in a vertical orientation remote from the table system. The actuator 152 includes a cylinder 154 enclosing a piston 156. In this embodiment, one side of piston 156 is attached to a rigid rod 158 extending beyond one end of cylinder 154 through suitable fluid seal means. The master actuator 152 is interconnected to the slave actuator 150 for fluid communication between the two via pressure connection line 160 and fluid return line 162. Lines 160, 162 are respectively connected to the actuators through coupling ports on the opposing ends of actuators 150, 152.

A cable connection clamp 164 is fixedly attached to the end of rod 158 extending beyond cylinder 154. One end of a flexible cable means 166 is attached to clamp 164 and extends over and around pulley 168. The other end of cable means 166 is attached to balancing weights 170 and suspends the weights against gravity.

In operation, the downward force (arrow 172) created by gravitational pull on the hanging weights is translated to an upward force (arrow 174) of equal magnitude on rod 158 via cable 166 and pulley 168. The upward force on rod 158 causes piston 156 to pressurize the fluid in master actuator 152. Pressurized fluid flows through pressure connection line 160 to slave actuator 150 causing a force to be exerted against the slave actuator piston of sufficient magnitude to balance the weight to be counter-balanced.

A solenoid valve 176 is interposed in pressure connection line 160 to selectively prevent fluid flow in line 160. This allows the operator to lock the moving structure in place once the desired position is achieved.

It is to be reiterated that the various embodiments of the present invention will find utility in various applications Diagnostic imaging systems include many components which are movable with respect to other structures. Whenever the movable structure is counterbalanced or a power assist is desirable, the present invention can be adapted for use by one skilled in the art. In addition, the invention has been described with reference to the preferred embodiment. Obviously, modifications and alterations will occur to others upon reading and understanding the preceding detailed description. It is intended that the invention be construed as including all such alterations and modifications insofar as they come within the scope of the appended claims or the equivalents thereof.

Having thus described the preferred embodiment, the invention is now claimed to be:

1. In a diagnostic imaging system comprising a penetrating radiation source, an image detector, and a fluid powered power-assist system, said fluid powered power-assist system comprising:
   (a) a first member;
   (b) a second member movably mounted to said first member;
   (c) a slave actuator comprising a cylinder having a first end and a second end and a reciprocating piston having a first side and a second side coupled between said first and second members, said slave actuator cylinder having a fluid coupling port located at each of said first and second ends of said slave actuator cylinder for coupling working fluid to each of said first and second sides of said slave actuator piston;
   (d) first and second master actuators each comprising a respective master actuator cylinder having a first end and a second end having a fluid coupling port located at each of said first and second ends of said first and second master actuator cylinders for coupling working fluid to said first end of each of said cylinders of said first and second master actuators and control fluid to said second end of each of said cylinders of said first and second master actuators;
   (e) working fluid connection lines connecting a coupling port of said first end of said cylinder of said slave actuator to a coupling port of said first end of said cylinder of the first master actuator and connecting a coupling port on the second end of said cylinder of said slave actuator to a coupling port of the second master actuator for providing working fluid flow between said first and second master actuators;
   (f) a control fluid pressure source;
   (g) control fluid pressure connection lines individually connecting the respective coupling port on each of the second ends of the respective cylinder of said first and second master actuators to said control fluid pressure source;
   (h) control means for producing first and second pressure signals in response to operator exerted force upon said control means such that said first and second pressure signals are simultaneously proportional to the operator exerted force; and
   (i) first and second pressure regulator means respectively interposed in said control fluid pressure connection lines corresponding to first and second master actuators, said pressure regulator means receiving the first and second pressure signals from the control means, for controlling the pressure to the master actuators as a function of the force exerted on said control means.

2. The system of claim 1 wherein the first member comprises an x-ray table body assembly and the second member comprises a vertical tower assembly.

3. The system of claim 1 wherein the first member comprises an x-ray table body assembly and the second member comprises a cassette carriage assembly 4. The system of claim 1 wherein the first member comprises a vertical tower assembly and the second member comprises an imaging system support frame assembly.

5. The system of claim 1 wherein the first member comprises an imaging system support frame assembly and the second member comprises a fluoroscopic imaging system.

6. The system of claim 1 wherein the cylinder of said slave actuator is secured to said first member and the piston of said slave actuator is secured to said second member.

7. The system of claim 1 additionally comprising a main valve means interposed in each of the working fluid connection lines for selectively preventing fluid flow in each of said working fluid lines.

8. The system of claim 7 additionally comprising means to selectively activate said main valve means.

9. The system of claim 1 wherein said control means comprises;
   (a) a power assist actuator including a power assist cylinder having a first and second end, a reciprocating power assist piston mounted in the power assist cylinder and a fluid coupling port located at each of said first and second ends of the power assist cylinder for hydraulically coupling said power assist actuator to said first and second pressure regulator means;
   (b) bias means coupled to the piston for maintaining the piston in a null position; and
   (c) handle means mounted in operative association with the bias means such that a force exerted on said handle causes said bias means to move said piston from its null position.

10. The system of claim 1 wherein said first and second pressure regulator means receive a first and second pressure feedback signal from said working fluid lines.

11. The system of claim 10 wherein additionally comprising feedback valve means for selectively blocking said first and second feedback signals.

12. The system of claim 1 wherein the working fluid is water and the control fluid is air.

13. In a diagnostic imaging system comprising a penetrating radiation source, and image detector, and a fluid powered counterbalance system, said fluid powered counterbalance system comprising;
   (a) a first member;
   (b) a second member movably mounted to said first member;
   (c) a slave actuator comprising a cylinder having a first end and a second end and a reciprocating piston having a first side and a second side coupled between said first and second members, said slave actuator cylinder having a fluid coupling port located at each of said first and second ends of said slave actuator cylinder for coupling a first fluid to each of said first and second sides of said slave actuator piston;
   (d) first and second master actuators each comprising a respective master actuator cylinder having a first side and a second side, said respective master actuator cylinders having a fluid coupling port selectively located at each of said first and second sides of said first and second master actuator cylinders for coupling the first fluid to said first side of each of said cylinders of said first and second master actuators and a second fluid to second side of each of said cylinders of said first and second master actuators;
   (e) fluid lines connecting a coupling port on said first side of said cylinder of said slave actuator to a coupling port of said first side of said first master actuator and connecting a coupling port on the second side of said cylinder of said slave actuator to a coupling port of said first side of the cylinder of said second master actuator;
   (f) a pressurized source of said second fluid;
   (g) fluid pressure lines individually connecting the respective coupling port at each of the second sides of the respective cylinder of said first and second master actuators to said second fluid pressure source;
   (h) first and second pressure feedback lines respectively connected to the first sides of the respective cylinders of said first and second master actuators; and
   (i) first and second pressure regulator means respectively interposed in said second fluid pressure connecting lines, said regulator means respectively receiving said first and second pressure feedback lines for controlling the pressure of the second fluid to the master actuators as a function of the pressure of the first fluid in the first fluid connecting lines.

14. The system of claim 13 additionally including a power assist apparatus comprising;
   (a) control means for producing first and second pressure signals in response to operator exerted force upon said control means, said first and second pressure signals being proportional to the operator exerted force; and
   (B) means to communicate said first and second pressure signals respectively to said first and second pressure regulator means for controlling the pressure to the master actuators as a function of the operator exerted force.

15. The system of claim 14 wherein said control means comprises:
   (a) a power assist actuator including a power assist cylinder having a first end and a second end, a reciprocating power assist piston mounted in the power assist cylinder and a fluid coupling port located at each of said first and second ends of the power assist cylinder for hydraulically coupling said power assist actuator to said first and second pressure regulator means;
   (b) bias means coupled to the piston for maintaining the piston in a null position; and
   (c) handle means mounted in operative association with the bias means such that a force exerted on said handle causes said bias means to move said piston from its null position.

16. In a diagnostic x-ray imaging system comprising an x-ray source, an x-ray image detector, and a hydraulic counterbalance system, said hydraulic counterbalance system, comprising:
   (a) first member;
   (b) a second member movably mounted to said first member;
   (c) a slave actuator comprising a slave actuator cylinder having a first end and a second end and a reciprocating slave actuator piston selectively coupled between said first and second members, said slave actuator having a fluid coupling port located on at least a first end of said slave actuator cylinder for coupling actuating fluid to one side of said slave actuator piston;

(d) a master actuator comprising a master actuator cylinder, a reciprocal master actuator piston and a fluid coupling port located on at least a first end of said master actuator cylinder for coupling actuating fluid to one side of said master actuator piston;
(e) means for connecting said fluid coupling ports for fluid communication between said master and slave actuators;
(f) piston extension means having a first end secured to a second side of said master actuator piston and an extending end extending beyond a second end of said master actuator cylinder;
(g) balancing weight means coupled to the extending end of said piston extension means causing said piston to exert pressure on said actuating fluid; and
(h) wherein said master actuator and said balancing weight means are located remote from said first and second members.

17. The system of claim 16 additionally comprising valve means interposed in said fluid connecting means for selectively preventing fluid communication between said master actuator and slave actuator cylinders.

18. In a diagnostic imaging system comprising a penetrating radiation source, an image detector, and a fluid powered power-assist system, said fluid powered power-assist system comprising:
(a) a first member;
(b) a second member movably mounted to said first member;
(c) a slave actuator comprising a cylinder having a first end and a second end and a reciprocating piston having a first side and a second side coupled between said first and second members, said cylinder having a fluid coupling port located at each of said first and second ends of said cylinder for coupling working fluid to each of said first and second sides of said piston;
(d) control means for producing first and second pressure signals in response to operator exerted force upon said control means, such that said first and second pressure signals are simultaneously proportional to the operator exerted force; and
(e) master power control means receiving said first and second pressure signals and further connected to the fluid coupling ports of said slave actuator for creating a working fluid pressure differential across the reciprocating piston in response to said first and second pressure signals.

19. In a diagnostic imaging system comprising a penetrating radiation source, an image detector, and a fluid powered counterbalance system, said fluid powered counterbalance system comprising:
(a) a first member;
(b) a second member movably mounted to said first member;
(c) a slave actuator comprising a cylinder having a first end and a second end and a reciprocating piston side and a second side coupled between said first and second members, said cylinder having a fluid coupling port located at each of said first and second ends of said cylinder for coupling working fluid to each of said first and second sides of said piston;
(d) master power control means connected to the fluid coupling ports of said slave actuator, said master power control means comprising:
(i) pressure feedback means for sampling working fluid pressure on each of said first and second sides of said piston and for producing first and second pressure feedback signals; and
(ii) regulator means receiving said first and second pressure feedback signals and controlling the working fluid pressure on each of said first and second sides of said piston in response thereto.

* * * * *